US006752796B2

(12) United States Patent
Karami

(10) Patent No.: US 6,752,796 B2
(45) Date of Patent: Jun. 22, 2004

(54) DISPOSABLE PANT TYPE ABSORBENT ARTICLE

(75) Inventor: Hamzeh Karami, Lockhaven, PA (US)

(73) Assignee: First Quality Products, Inc., Great Neck, NY (US)

( * ) Notice: Subject to any disclaimer, the term of this patent is extended or adjusted under 35 U.S.C. 154(b) by 5 days.

(21) Appl. No.: 09/965,381

(22) Filed: Sep. 27, 2001

(65) Prior Publication Data

US 2002/0045879 A1 Apr. 18, 2002

Related U.S. Application Data

(63) Continuation-in-part of application No. 09/247,629, filed on Feb. 10, 1999, and a continuation-in-part of application No. 09/844,726, filed on Apr. 27, 2001.

(51) Int. Cl.[7] ............................................... A61F 13/15
(52) U.S. Cl. ...................... 604/391; 604/390; 604/393; 604/386; 604/394
(58) Field of Search ........................... 604/386, 387, 604/392, 393, 394, 396, 385.01, 391, 390

(56) References Cited

U.S. PATENT DOCUMENTS 5,087,253 A * 2/1992 Cooper ................. 604/385.15
5,403,303 A * 4/1995 Beplate ........................ 604/394
6,264,643 B1 * 7/2001 Toyoda .................. 604/385.29
6,447,497 B1 * 9/2002 Olson .......................... 604/389
2003/0130641 A1 * 7/2003 Richlen et al. ......... 604/385.01

* cited by examiner

Primary Examiner—John J. Calvert
Assistant Examiner—Jacqueline F Stephens
(74) Attorney, Agent, or Firm—Amster, Rothstein & Ebenstein LLP

(57) ABSTRACT

A ready-to-wear pull-up type absorbent article such as a diaper is provided which has a waist region comprising a front waist region and a back waist region, and a pair of complimentary fasteners in the respective regions. The front waist region comprises a pair of loop fasteners and the back waist region comprises a pair of hook strips each aligned for releasable engagement with a corresponding loop strip in the front waist region. In lieu of hook strips, the back waist region may include one or more tape tabs each having one surface attached to the back waist region and an opposed hook surface for releasable engagement with a correspondingly aligned loop surface. A weakened line, e.g., a perforated line may be provided in the front waist region which can be readily torn away in order to inspect the diaper. The front and back waist regions may include side seals which can be secured together when the diaper is in assembled ready-to-wear condition and which can be readily torn or peeled in order to inspect the diaper when desired without disengaging the fasteners.

10 Claims, 16 Drawing Sheets

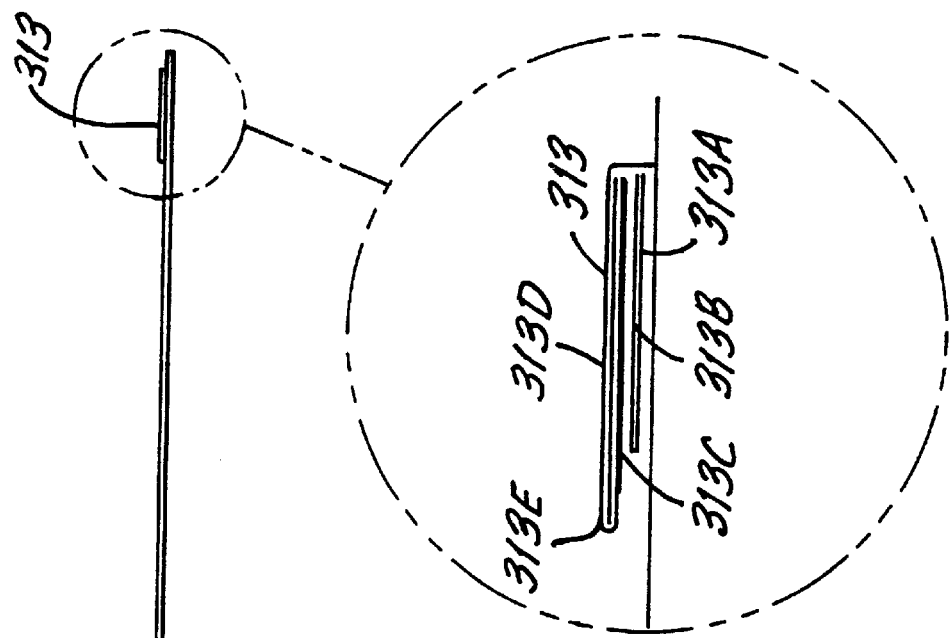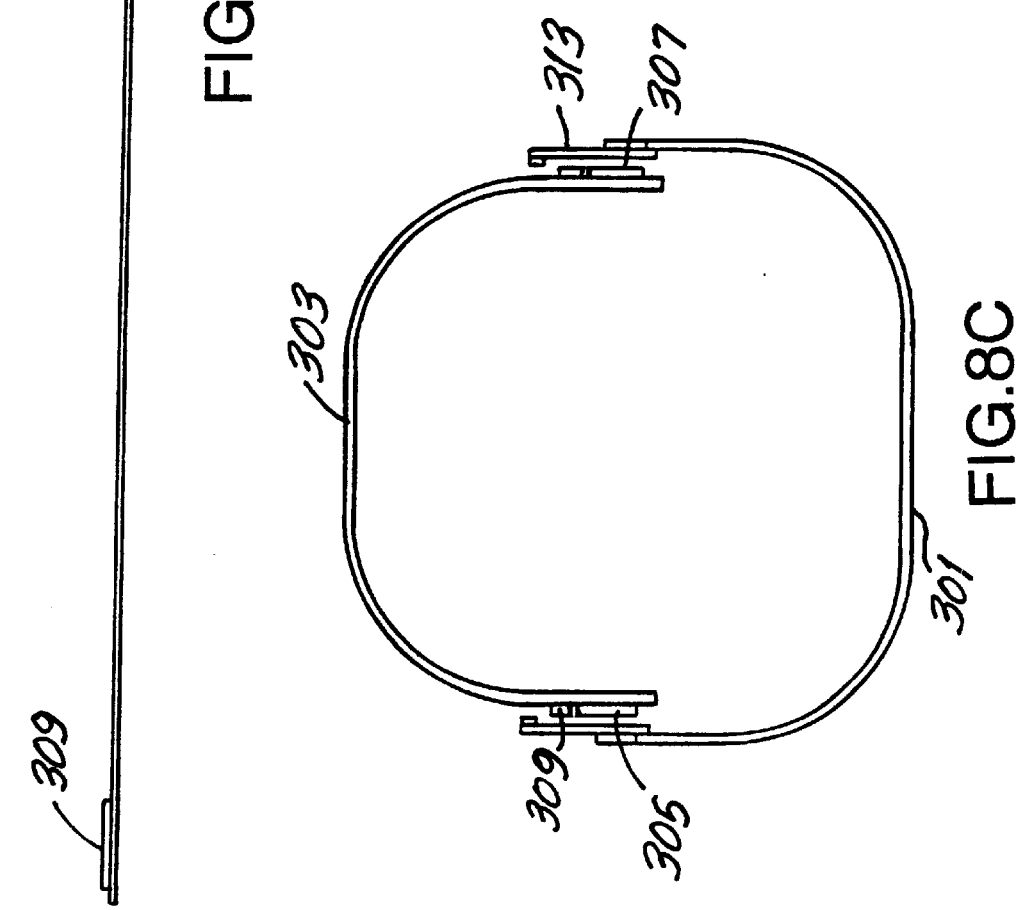

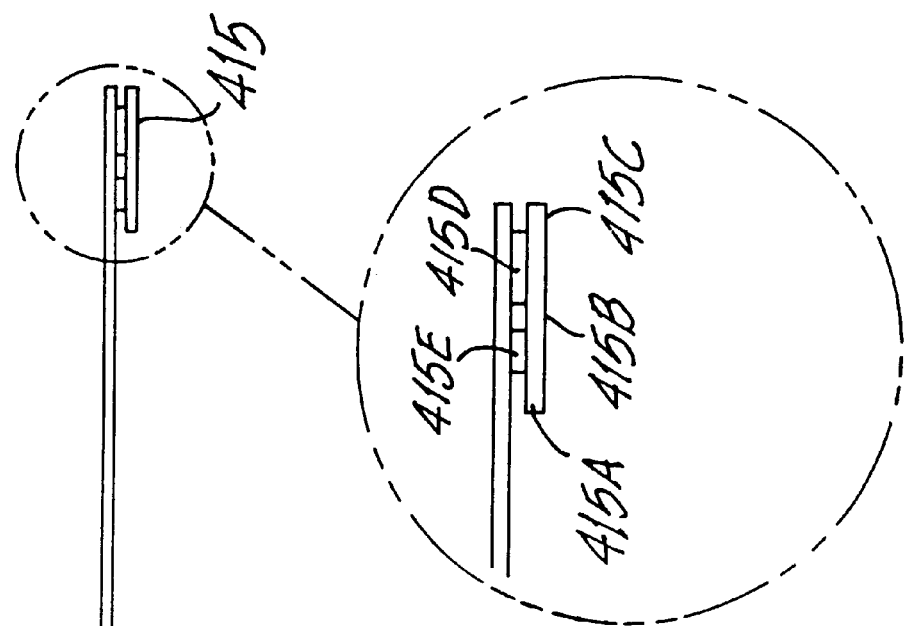
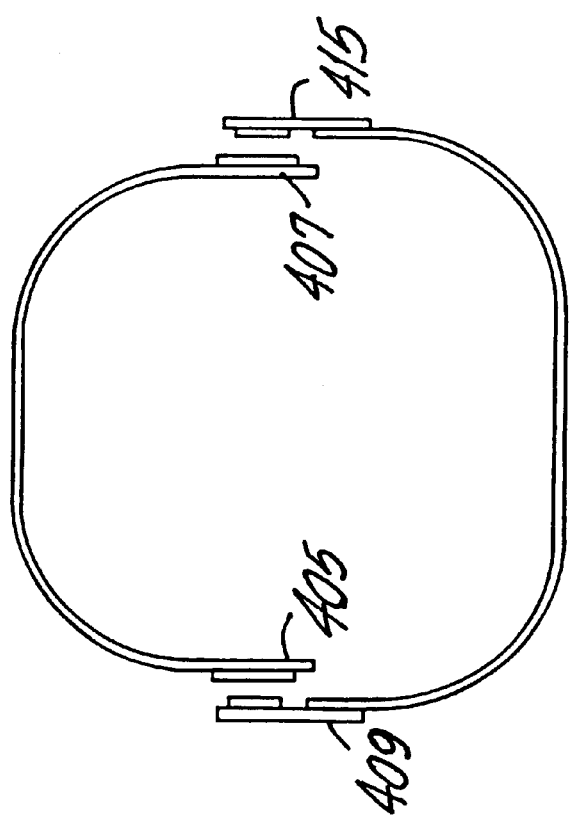

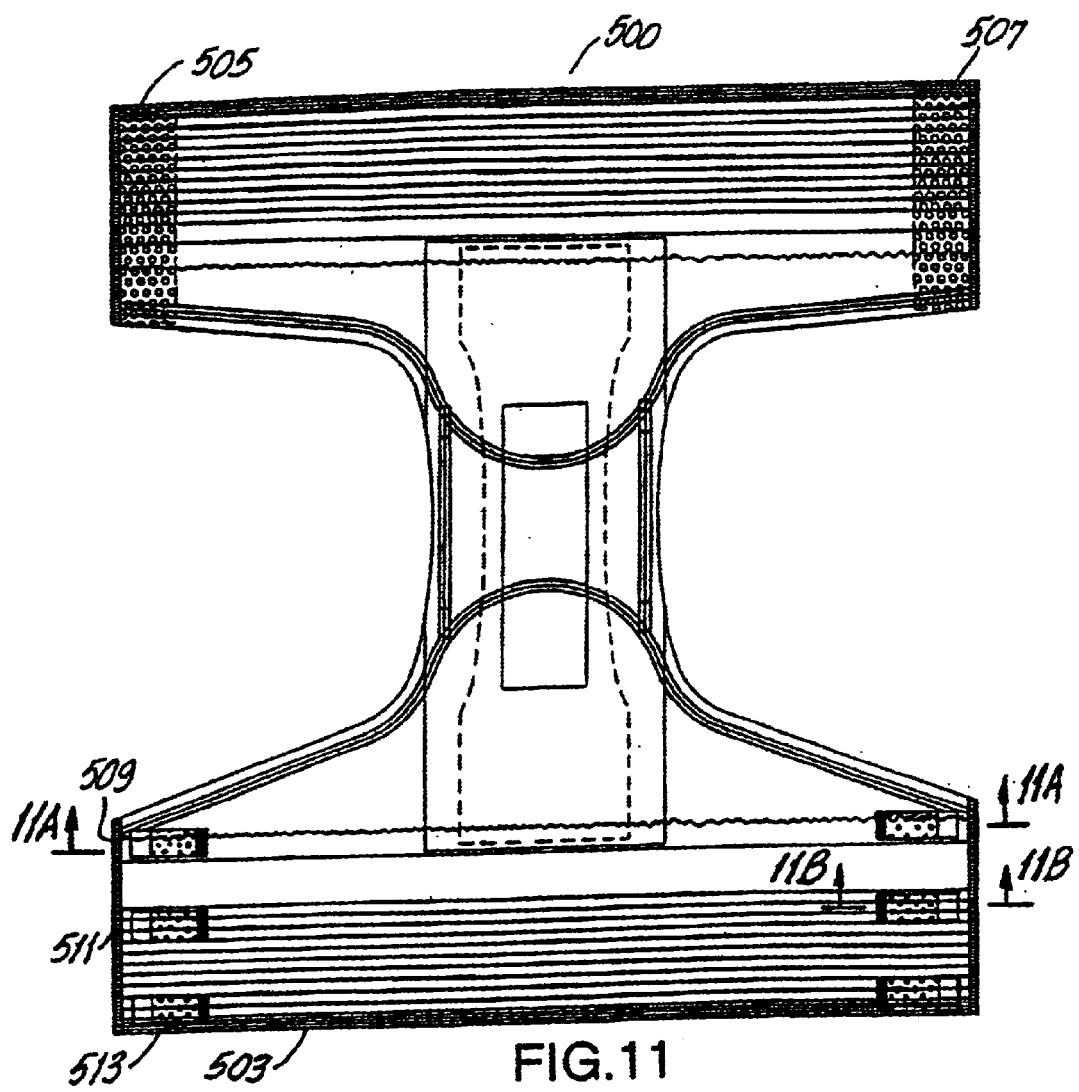
FIG.11
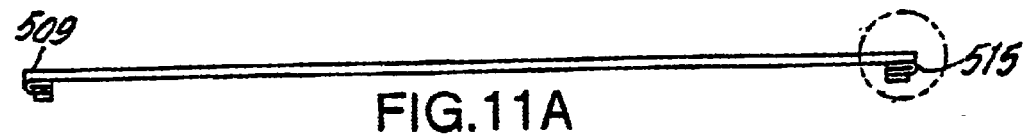
FIG.11A
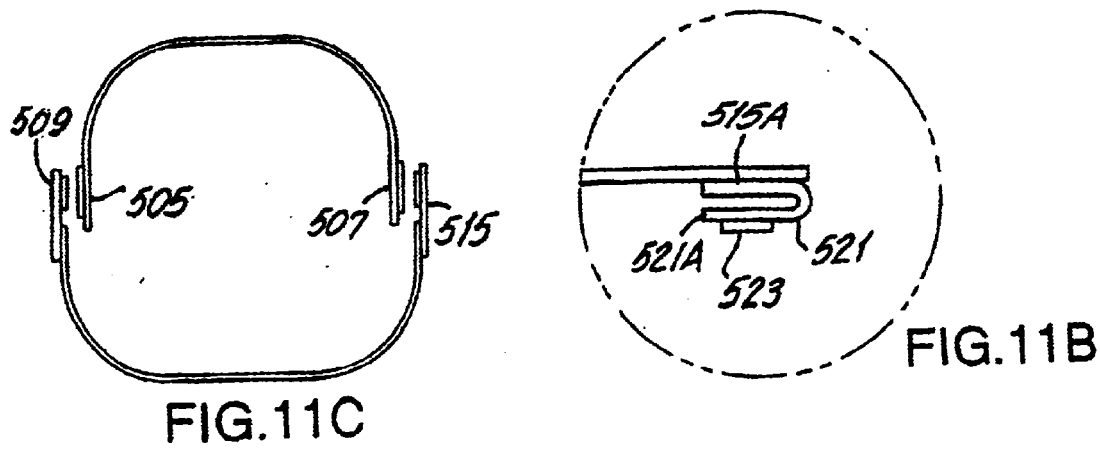
FIG.11C
FIG.11B

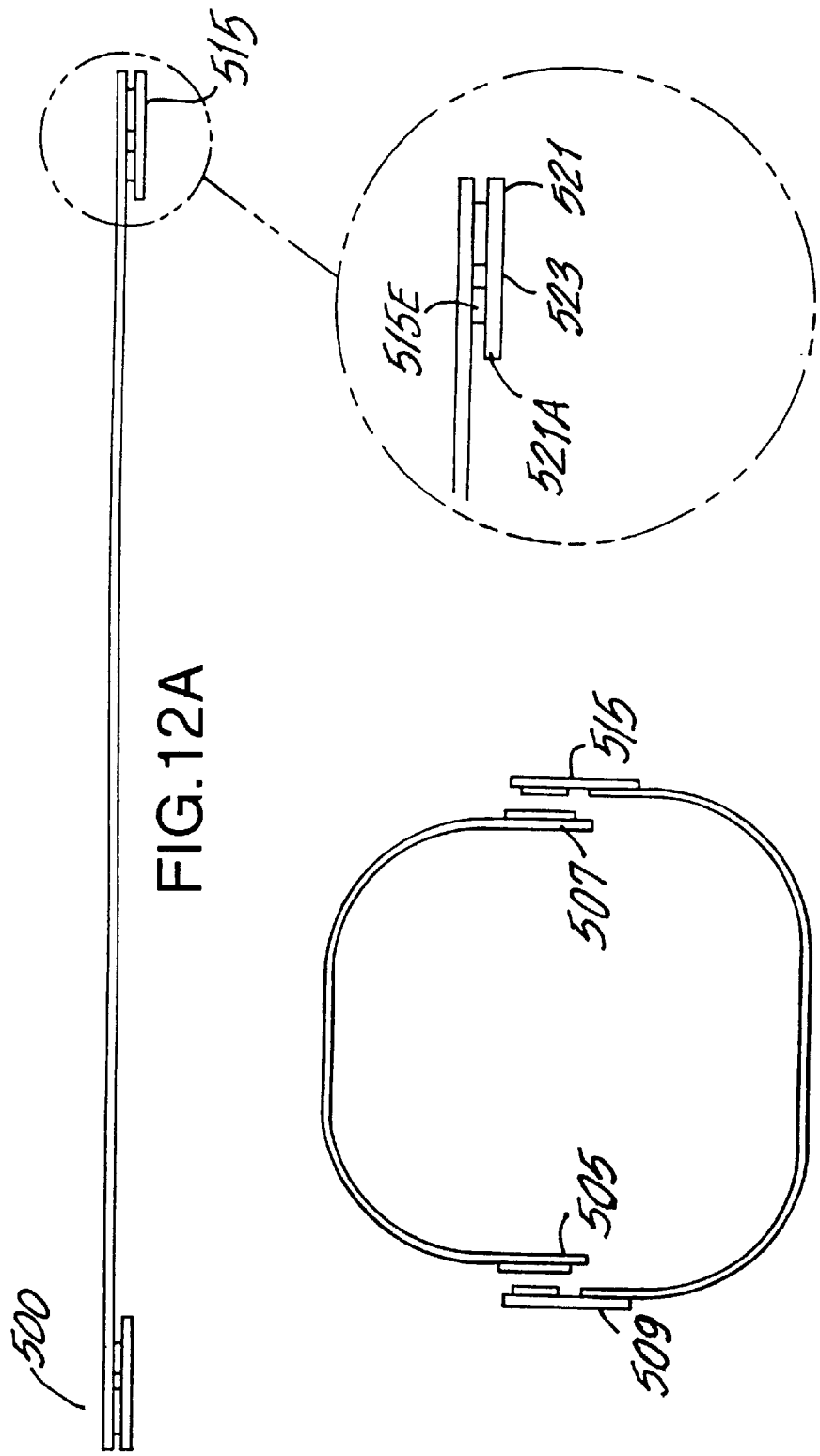

DISPOSABLE PANT TYPE ABSORBENT ARTICLE

RELATED APPLICATION

This application is a continuation-in-part of commonly assigned, copending application Ser. No. 09/247,629 filed Feb. 10, 1999 for Disposable Absorbent Pull-Up Type Diapers And Incontinent Briefs, and Ser. No. 09/844,726 filed Apr. 27, 2001 for Absorbent Articles Having Improved Fastening System.

FIELD OF THE INVENTION

The present invention relates generally to disposable absorbent articles such as training pants, diapers, undergarments and incontinent briefs, and is more particularly related to such pants, diapers, undergarments and briefs which have become known in the art as "pull-up" or "pull-on" absorbent articles. In one particular aspect, the present invention relates to an absorbent article of the aforementioned types which, due to its unique construction, assures fitness and comfort to the wearer, protects against leakage of fluids and other body exudates and can be readily opened for inspection and removal from the wearer. This invention also relates to ready-to-wear pull-up type absorbent articles.

BACKGROUND OF THE INVENTION

Disposable absorbent articles such as disposable baby diapers and adult incontinent briefs, underpants, guards and the like articles are widely used in homes and in various health care facilities and institutions. Indeed the use of such articles has become a common sanitary practice, and while initially such absorbent articles were used mostly for infant care, more recently their use has been expanded to include adults as well. In both instances, the absorbent article must be designed to effectively prevent leakage of urine and other fecal materials, while insuring body fit and comfort.

Most presently available absorbent articles are generally unitary in structure, pre-shaped and pre-folded, and comprise an absorbent pad having a liquid permeable top sheet facing the wearer's body, a liquid impermeable backsheet on the opposite side, and an absorbent sheet or panel disposed between the top sheet and the back sheet. The absorbent article comprises a front side portion, a crotch portion and a backside portion, and further includes elastic members along the circumference of the waist and around the leg openings. While the heretofore commercially available absorbent articles have been somewhat effective against leakage of body fluids and fecal materials, and have therefore met some degree of acceptability, they have not been entirely satisfactory for their intended applications. In other words, they have not proven to be entirely leak proof, nor have they completely prevented issuance of the body exudates outside the diaper or the underpants. These deficiencies are primarily due to inadequate and loose body fit, which result in leakage of the body fluids and solids through the legs' openings. These problems are even more pronounced in case of adults because of their diverse body shapes and varying contours. Another disadvantage of the commercially available absorbent articles such as diapers, incontinent briefs and the like, is associated with opening and removing the soiled article for inspection without soiling the wearer's leg or body, or changing the diaper while the wearer has his or her shoes and pants on.

There are several patents which disclose various attempts made in the prior art over the past years to eliminate, or at least minimize, the shortcomings of the present commercially available absorbent briefs. Some of these patents are referred to in the aforementioned commonly assigned, copending application. That application describes a pull-up diaper comprising front and back elasticized waist portions, an insert member having an absorbent core comprising an elasticated crotch region, and at least one elastic member disposed in the longitudinal direction on each side of the crotch region. As shown in FIGS. 1 and 2 of said copending application, the diaper is provided with side seals formed by heat, pressure or combination thereof. In addition, a finite area at each end of the side seals is sealed adhesively or by a hot melt. In an alternative embodiment shown in FIG. 2C of said copending application, male and female Velcro® regions are provided which are adapted to engage into one another to provide a seal when the front portion of the diaper is folded on the back portion of the diaper.

In a recent patent, i.e., U.S. Pat. No. 6,027,484 issued Feb. 22, 2000 to Anette Remare, a pant diaper is described comprising a piece of fibrous nonwoven or plastic elastic material 9 having two parts 13 and 14 which can be pulled apart to define the side parts or flaps of the diaper. The side parts are fastened together by means of the hooks 15, 16 and the loop 17 as shown in FIGS. 1 and 2. The piece 9 is joined to the outer casing 3 of the front part of the diaper by the glue points 10 which may be homogeneously distributed as shown in FIG. 1 or non-homogenous glue points or fastening means 110 as shown in FIG. 3.

A more recent patent, i.e., U.S. Pat. No. 6,287,287 B1 describes a prefastened disposable article which includes a pair of primary fasteners located on opposed side edges of one waist region. The primary fasteners overlap and releasably engage the opposite waist region. A pair of passive bonds releasably connect the overlapped portion of one waist portion to the opposite waist region in order to maintain the article in prefastened condition.

In general, the briefs and diapers described in the prior art patents have a common structural deficiency in that they are provided with side seams which are welded together by heat and pressure or vibration (ultrasonic welding). Side seals must be sufficiently strong to hold the diaper on the person and must be capable of being torn so that the wearer can tear it easily in order to inspect or change the diaper while having his or her shoes on. Thus, there is a dire need for pull up type absorbent briefs and diapers which are comfortable to wear, highly effective against leakage of fluids and feces, and which can be readily inspected for soil.

Accordingly, it is an object of the present invention to provide a pull-up type disposable absorbent article such as infant diapers, adult incontinent underpants, briefs, guards and the like articles, which overcome the deficiencies and shortcomings of the prior art absorbent articles, including present commercially available garments used for this purpose.

It is another object of this invention to provide disposable absorbent articles which, due to their unique construction, provide improved fit to the body and prevent leakage of urine and other body exudates through the leg openings, and which are easy to take apart for inspection.

It is also an object of this invention to provide such disposable articles which, due to their unique side seals and fastener system, are easy to open up for inspection and which can be readily reassembled after inspection even while the wearer has his or her shoes on.

The foregoing and other objects and features of the present invention will be more fully comprehended and appreciated from the ensuing detailed description and drawing which form parts of this application.

It must be understood throughout this application that the term "pull-up" as used herein is synonymous with "pull-on" as used in the prior art patents.

SUMMARY OF THE INVENTION

The present invention is concerned with providing a ready-to-wear absorbent article such as, for example, a diaper. The diaper comprises a cover sheet, a back sheet, an absorbent layer disposed intermediate the cover sheet and the back sheet, a pair of opposed leg openings and a waist region. The waist region comprises a front waist region and a back waist region connected to each other by a crotch portion, and has belly section which may be elasticated. The front and back waist regions are provided with fasteners for fastening the two regions together. In one embodiment, the fastening system comprises a pair of loop strips in the front waist region, and a pair of correspondingly aligned hook strips in the back waist region such that when the back waist region and front waist region are overlapped, each hook strip releasably engages a correspondingly aligned loop strip. In lieu of a loop strip, the surface of the front waist region itself may act as a loop or a female surface, or a selected segment of the surface may act as the loop for engagement with the hook (male) strip. The front waist region may include a weakened line such as a perforated line adjacent to or in between the strips which can be readily torn in order to inspect the diaper without disengaging the hook and loop fasteners.

In a variation of the invention, the back waist region comprises one or more tabs located at the lateral or side edges of the waist region. Each tab has one surface attached to the back waist region and an opposed hook surface aligned with a loop strip in the front waist region. In order to fasten the diaper, the back waist region and front waist region are overlapped so as to engage the hook surface of each tab with a correspondingly aligned loop surface.

BRIEF DESCRIPTION OF THE DRAWINGS

In the drawings, wherein like reference numerals are employed to designate like parts:

FIG. 8A is a cross-sectional view taken along the line 8A—8A of FIG. 8;

FIG. 8B is a cross-sectional view taken along the line 8B—8B of FIG. 8;

FIG. 8C is a view similar to FIG. 5 showing the overlapping of the front waist and the back waist of the diaper;

FIG. 10A is a cross-sectional view taken along the line 10A—10A of FIG. 10;

FIG. 10B is a cross-sectional view taken along the line 10B—10B of FIG. 10;

FIG. 10C is a view similar to FIG. 8C but showing the manner of fastening the front waist and back waist of the diaper shown in FIG. 10;

FIG. 11 is a stretched plan view of a different embodiment of the present invention similar to the embodiment illustrated in FIG. 11 with the tape tabs located on the outside surface of the back waist region, folded and adhesively secured to said surface;

FIG. 11A is a cross-sectional view taken along the lines 11A—11A of FIG. 11;

FIG. 11B is a cross-sectional view taken along the line 11B—11B of FIG. 11;

FIG. 11C is a view similar to FIG. 10C showing the overlapping the front waist and back waist of the diaper;

FIG. 12A is a cross-sectional view taken along the line 12A—12A of FIG. 12;

FIG. 12B is a cross-sectional view taken along the line 12B—12B of FIG. 12;

FIG. 12C is a view similar to FIG. 10C showing fastening system; and

DETAILED DESCRIPTION OF THE INVENTION

Figure 1:
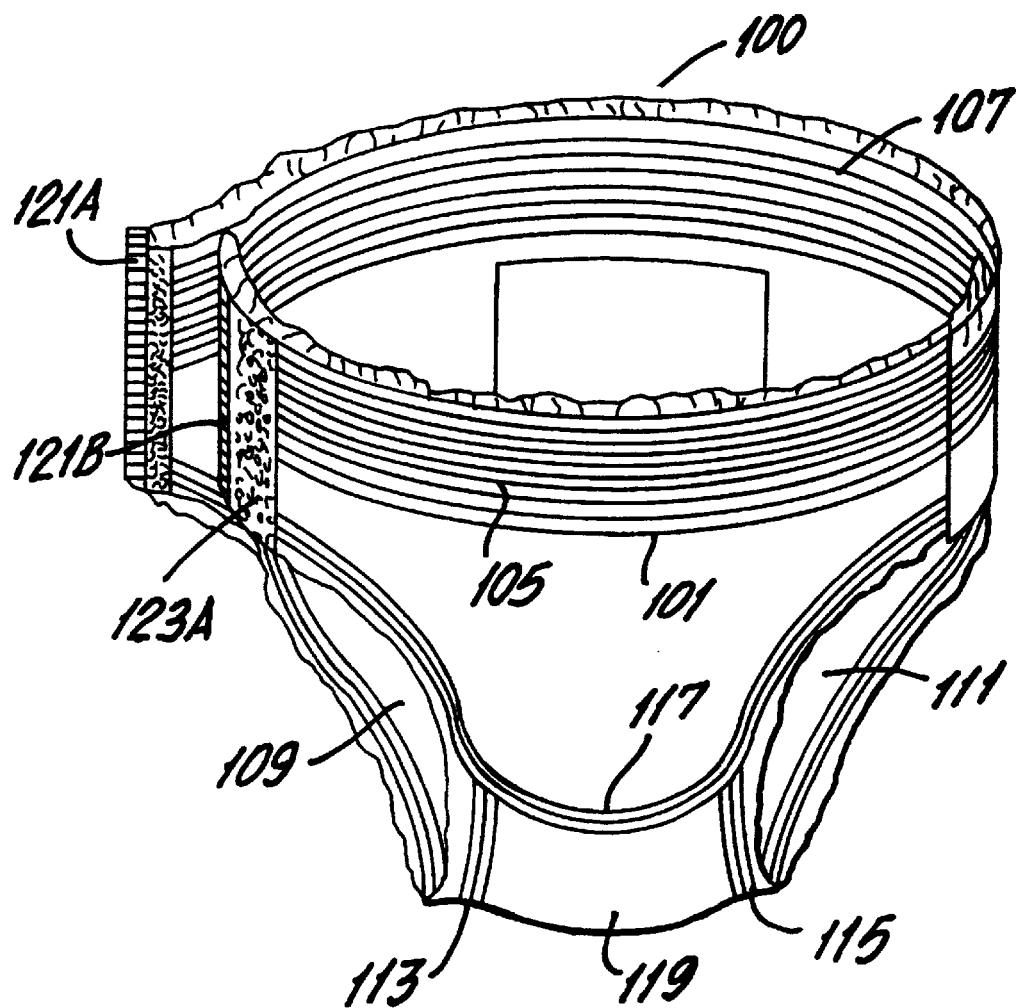
FIG. 1 is a perspective view of the disposable absorbent article of the present invention shown as a pull-up diaper having side seals which are broken apart on one side for illustrative purposes.
Figure 2:
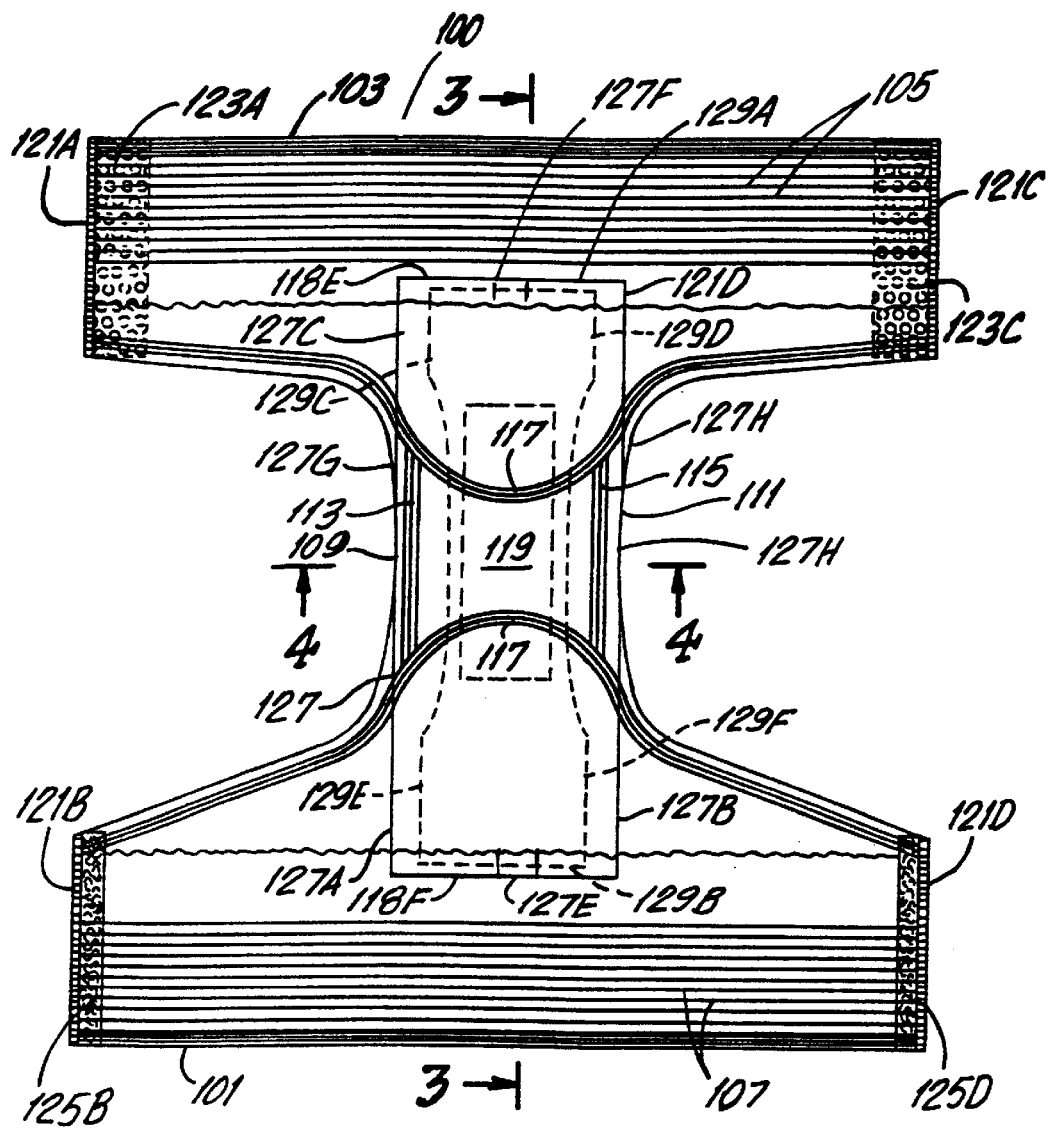
FIG. 2 is a stretched plan view of the pull-up diaper shown in FIG. 1.

Referring to FIG. 1, there is shown a pull-up diaper generally designated as 100 comprising an elasticated back waist region 101 and an elasticated front waist portion 103. The elasticated back waist region 101 includes an elastic band comprising a plurality of elastic members 105 spanned across the back waist region 101, and the elasticated front waist region 103 includes an elastic band comprising a plurality of elastic members 107 spanned across the front waist portion 103. The diaper 100 also comprises a pair of elasticated leg openings, i.e., a right elasticated leg opening 109 and a left elasticated leg opening 111. The right leg opening 109 is provided at its peripheral edges with the crotch elastic members 113 and the left leg opening 111 is also provided at its peripheral edges with the crotch elastic member 115. Each leg opening also comprises a thigh elastic member 117 which is usually tensioned from about 0 to about 400 percent elongation, preferably from about 150 to about 250 percent elongation. The peripheral crotch elastic members 113 and 115 may also tensioned from about 0 to about 400 percent elongation, preferably from about 200 to about 300 percent elongation so that the leg openings fit snugly against the crotch region 119 of the wearer in order to prevent leakage of urine or other body exudates through the leg openings. The front and back of the diaper 100 are provided with the side seals 121A, 121B disposed at the outer right edges of the back waist region 101 and the front waist region 103, and similar side seals 121C and 121D are disposed at the outer right edges of the front waist region 101 and the front waist region 103 as shown in FIG. 2. These side seals may be formed by heat, pressure, combination of heat and pressure, or by a suitable adhesive in a manner known in the prior art. The side seals preferably have low peel strength so that when the seals are torn or peeled away their external edges remain clean. Preferably, the side seals strength may be from 1 to about 3 pounds per inch, and more preferably less than about 1 pound per inch.

The diaper may also be provided with elastics at the belly portion in the front or back but such belly elastics are not strictly necessary for some diapers.

Ordinarily, in order to inspect the diaper during wear, the seal is ripped open and the diaper is inspected for the presence of feces or exudates. Once inspected, the diaper is disposed of since it is often difficult to effectively reseal the side seals. In the embodiment of the present invention shown in FIG. 2, the diaper is provided with two strips of hook and loop material 123A, 123C disposed adjacent the side seals 121A and 121C. Both the side seals and the strips of the loop fastener material are disposed parallel to the vertical axis of the diaper. Similarly, strips of hook material 125B, 125D are disposed adjacent the side seals 121B, 121D, parallel to the vertical axis of the diaper. During use, when the front and back portions of the diaper are folded, the hook strips 125B and 125D engage onto the loop strips 123A and 123C, respectively thus providing additional sealed regions at the lateral edges of the front waist portion and the back waist portion. This construction permits opening the diaper for inspection by disengaging the hook and loop strips 123A and 125B, or the hook and loop strips 123C and 125D in order to inspect the diaper. If no feces or exudates are found, the diaper is closed, i.e., resealed by re-engaging the hook and loop strips without disposing of the diaper. FIG. 1 shows the diaper during wear with one edge partially open and the hook and loop strips in disengaged positions. It is preferable that the loop strips be located inside surface the hook be located on the outer surface of the diaper.

Referring again to the drawings, more specifically to FIGS. 2–5, the diaper 100 comprises an insert member 127 which contains the absorbent core 129 sandwiched between the cover or top layer or sheet 131 (facing the body of the wearer) and the polyethylene backing film 133. The insert 127 is secured, adhesively or by some other suitable means, to a spunbond nonwoven layer 135. Optionally, the absorbent core 129 may be covered by the bottom tissue layers 137 generally made of wood pulp fibers or similar material. An acquisition layer 139 is interposed between the cover sheet 131 and the core layer 129 and serves to temporarily retain the body exudates and slowly distribute them through the absorbent core 129 in order to keep the skin dryer. The various layers are generally coextensive with one another and are sealed together to form a sealed composite structure.

As shown in FIG. 2, the absorbent core 129 spans substantial part of the length of the diaper 100 terminating at the back edge 129A, the front edge 129B, the right side edges 129C, 129D, and left side edges 129 and 129F. However, as it can also be seen from this figure, the back edge 129A and the front edge 129B of the absorbent core 129 are spaced apart a finite distance, which may be varied, relative to the diaper. The insert 127 is defined by the longitudinal side edges 127A, 127B, 127C and 127D, the lateral edges 127E and 127F, and includes the necked down region defined by the necked down contoured side edges 127G and 127H. The necked down region defined by the necked down side edges is elasticated at both sides by the elastic members 113, 115. Three elastic members are shown although fewer or greater numbers of elastic members may be used if desired.

As previously mentioned, each leg opening 109, 111 is tensioned by a thigh elastic member 117 shown as a curved elastic in FIG. 2, but may be straight elastic element if desired. The thigh elastic may be tensioned from about 0 to about 400 percent elongation, preferably from about 150 to about 300 percent elongation for more improved fitness around the legs.

As is further shown in FIG. 2, the diaper 100 of the present invention has an elasticized crotch region 119 which is provided with one or more spaced-apart right elastic members 113 disposed interiorly of the leg right opening 109 on the right side edge of the insert, and one or more spaced-apart left elastic members 115 disposed interiorly of the leg opening 111 of the left side of the insert 127.

Figure 3:
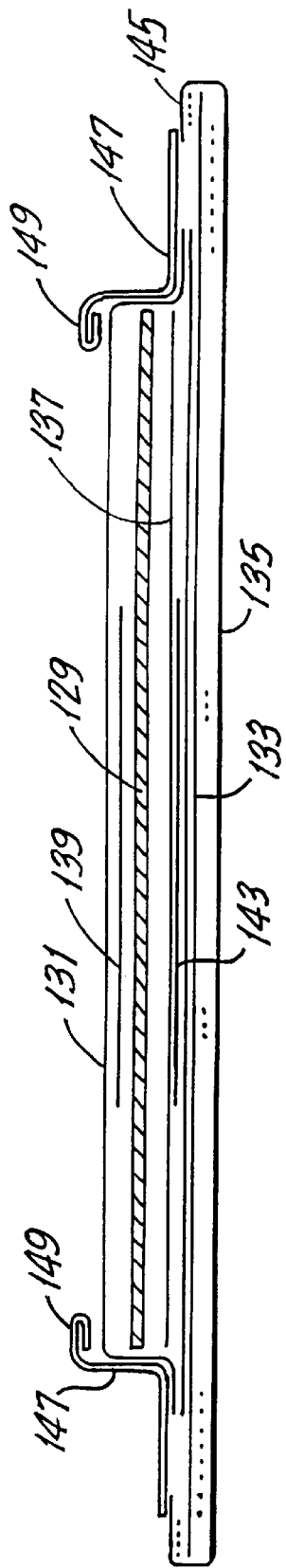
FIG. 3 is a sectional view taken along the line 3—3 of FIG. 2.
Figure 4:
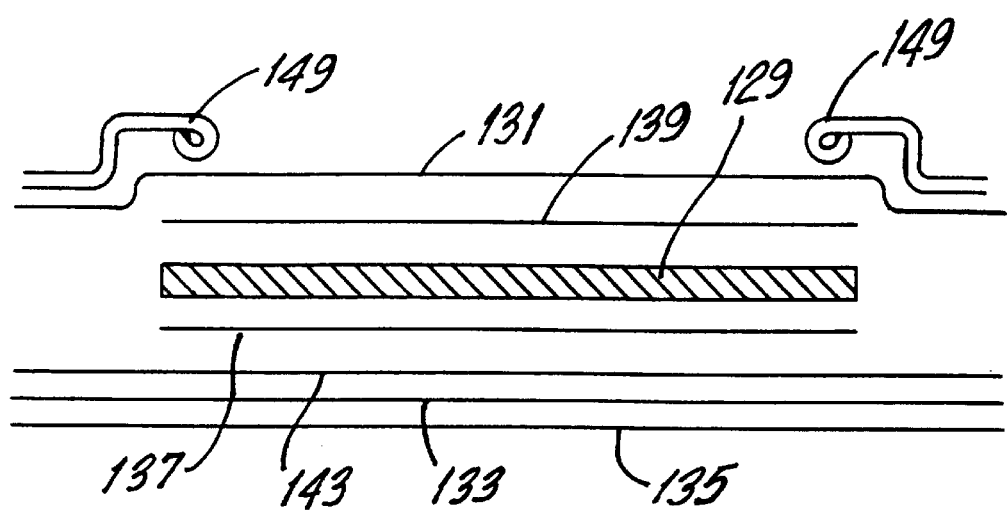
FIG. 4 is a sectional view taken along the line 4—4 of FIG. 2.
Figure 5:
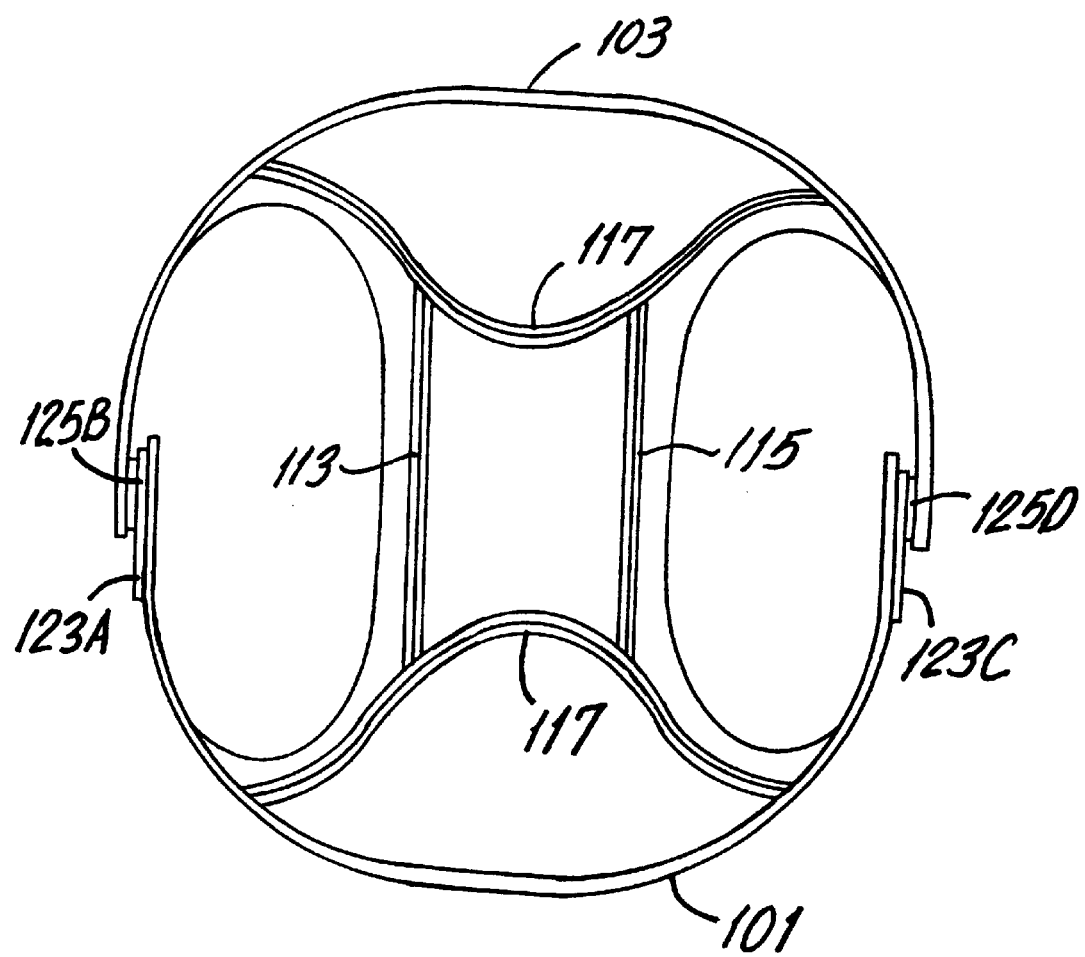
FIG. 5 is a schematic view illustrating overlapping of the front waist region and back waist region of the diaper shown in FIG. 1 and the manner of their attachment by hook and loop.

Referring to FIGS. 3 and 4, the coversheet or layer 131 is conveniently made of spunbond nonwoven polypropylene which is available from First Quality Fibers, Inc., McElhattan, Pa. The acquisition layer 139 is usually made of chemically bonded nonwoven polypropylene available from American Nonwovens, Columbus, Mo. Preferably, the width of this layer is substantially the same as the width of the absorbent core 129. This core may be made pulp fibers and superabsorbent polymers such as IM 7000 series available from Clariant Products, Inc., Portsmouth, Va., and Chemdal 200 series, available from Chemdal, Inc., Palantine, Ill. Alternatively, the absorbent core 129 may be made of dual layer construction, in which case, the absorbent polymer may be securely positioned between each layer of the absorbent material.

The film backing 133 is usually a polyethylene layer which is liquid, air and preferably vapor impermeable, and is placed under the absorbent core member 129 to prevent body exudates from leaking and otherwise soiling the user's bed and clothing. The width and length of the backing film 133 are generally at least equal to the width and length of the absorbent core 129. Polyethylenes suitable as backing film for the purpose of this invention are available from Clopay Plastics, Cincinnati, Ohio as is further shown in FIGS. 3 and 4, a layer 135 of spunbond nonwoven polypropylene is disposed as a backing layer and covers the area under the insert 127. This layer is usually coextensive with the overall width and length of the pull-up diaper.

As is further shown in FIGS. 2 and 3, there is one elasticated crotch cuff 143 on each side of the garment. Each of these crotch cuffs is formed of a layer of spunbond nonwoven polypropylene laminated by hot-melt adhesive or by heat, and forms a fluid and an air impermeable composite structure. The crotch cuffs are under no tension or are tensioned from about 100 to about 200 percent so that the garment can fit snugly against the body and prevent leakage of body fluids or exudates, without pinching the body of the wearer. Additionally, these cuffs act as barriers against fluid leakage on each side of the absorbent core.

The garment of the present invention also has an elasticated waist cuff 145 which, similar to crotch cuffs, is not tensioned or is minimally tensioned between about 1 to about 100 percent elongation in order to provide a tight body fit which is leak-proof without pinching the body or causing discomfort to the wearer.

The insert 127 is adhesively secured to the nonwoven backing film 133 and, as shown in FIG. 2, the crotch width of the insert 127 is narrower than its width at the waist. As previously mentioned, there are usually three elastic members 113, 115 on each side, although fewer or more elastic members can be used, as desired.

As is further shown in FIGS. 3 and 4, the pull-on diaper of this invention has a waist cuff base 147 with a waist cuff apex 149 on both the front and back of the article. Similar to the crotch cuffs, these waist cuffs prevent fluid leakage from the ends of the core members 129.

In the embodiment shown in FIG. 2, the hook and loop fastener strips are located adjacent the side seals. However, in a variation of this embodiment, the hook and loop fastener strips may be used without the side seals and put on the diaper without the wearer taking of his or her shoes or pants. When in use, the wearer may disengage the strips, inspect the diaper for leaks and/or exudates and if free from such materials, the hook and loop strips may be refastened. The hook and loop fasteners may be attached to the inside or outside of the diaper. However, it is preferable to attach the loops on the inside surface and the hooks on the outside surface since the hook material has a rough surface which would irritate the skin. If the diaper is provided with side seals, this seal may be torn and the hook and loop fasteners are used to fasten the diaper.

Figure 6:
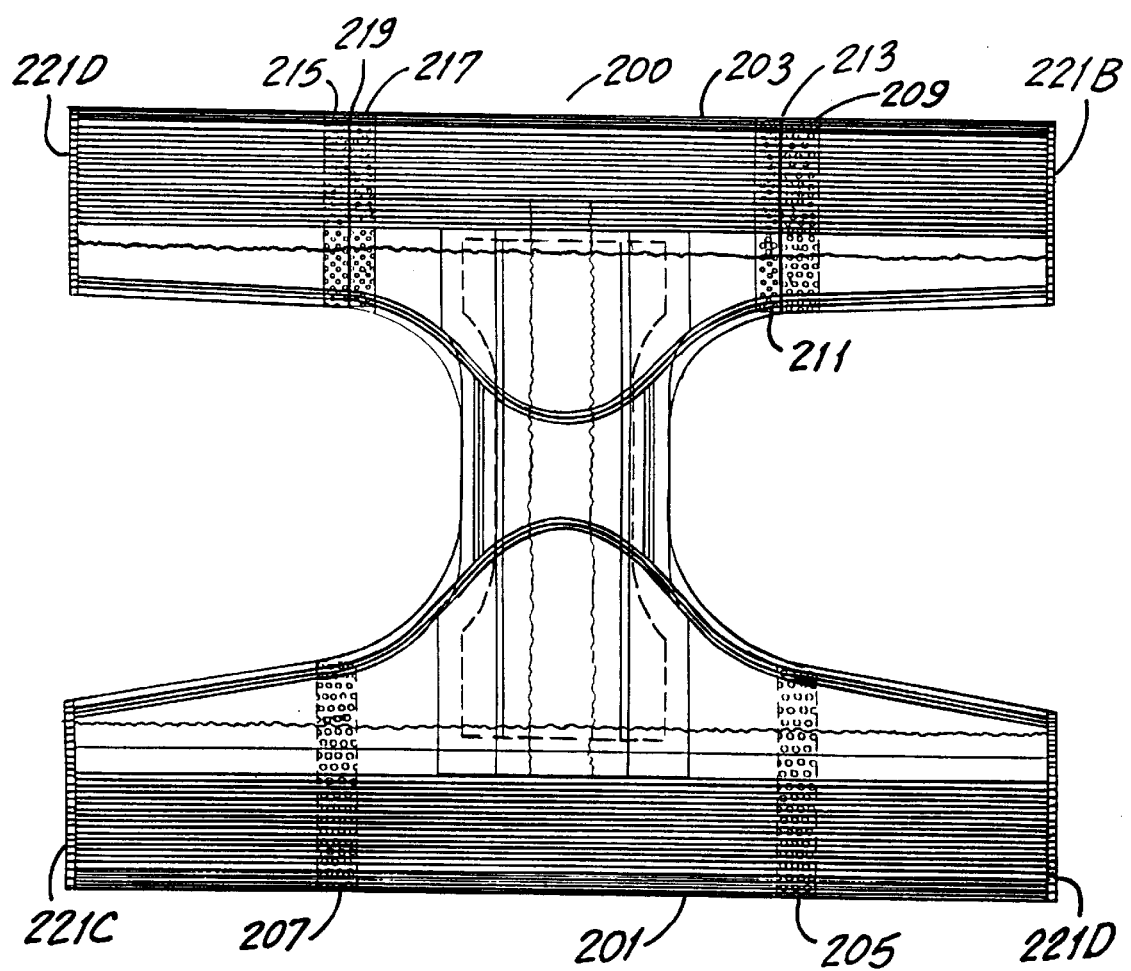
FIG. 6 is a stretched plan view similar to FIG. 2 but illustrating another variation of hook and loop fasteners.

Another variation of the fastening system for the diaper of this invention is shown in FIG. 6. The basic components of the diaper in this figure is the same as the diaper shown in FIG. 2 except for the number and location of the hook and loop strips. Thus, referring to FIG. 6, the front and back of the diaper 200 are provided with the side seals 221A, 221B disposed at the outer right edges of the back waist region 201 and the front waist region 203, and similar side seals 221C and 221D are located at the outer left edges of the back waist region 201 and the front waist region 203. These side seals may be formed by heat, pressure, combination of heat and pressure, or by a suitable adhesive in a manner known in the prior art. The back waist region 201 comprises a pair strips 205,207 of a loop material, with the loop strip 205 spaced apart inward relative to the edge or side seal 221D on the outer surface of the back waist region and the loop strip 207 spaced apart inward relative to the edge or side seal 221C on the outer surface of the back waist region. The term "strip" as used herein is not limited to any particular configuration as it may be rectangular, square, circular or any other shape and may be a patch or a section of the surface of material itself. Thus, the material itself may constitute a loop suitable for engagement with the hook strips. The front waist region 203 comprises the loop strip 209 spaced apart inward relative to the edge or side seal 221 B on the outer surface and a hook strip 211 on the inner surface adjacent the loop strip 209 and separated therefrom by a weakened tear line such as the perforated line 213. On the right side of the article, the front waist region comprises a pair of side-by-side hook strips 215,217 spaced apart inward relative to the edge or side seal 221A, and separated from each other by a weakened tear line such as the perforated line 219. Both hook strips 217,215 are located on the inner surface of the front waist region 203. In order to assemble and fasten the diaper, when the perforated lines 213 and 219 are torn and the front waist region 203 and back waist region 201 are folded on each other, the loop strip 209 engages the hook strip 215 around the waist and the hook strips 211 and 217 engage the loop strips 205 and 207, respectively. A segment of a nonwoven material or some other suitable material may be used as enforcement or backup portion for the perforated lines in order to assure a clean tear of the perforated line.

Figure 7:
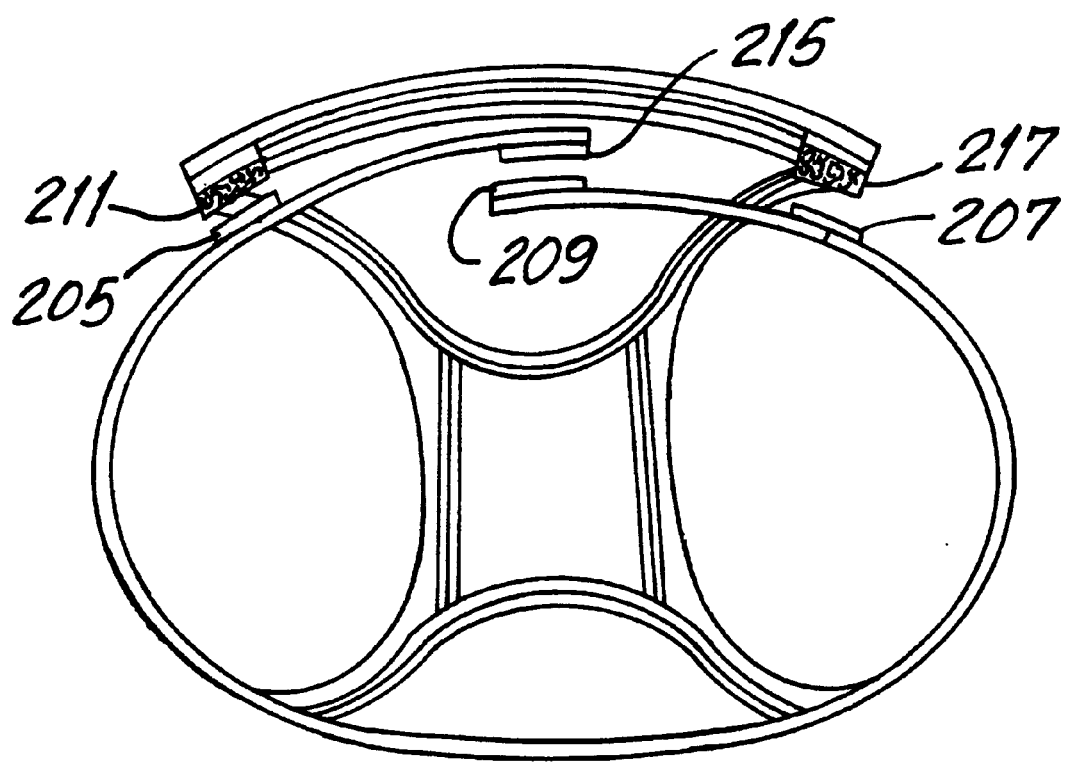
FIG. 7 is a schematic view similar to FIG. 5 but illustrating the hook and loop fastener arrangement in FIG. 6.

FIG. 7 is a schematic representation of the manner of fastening the hook and loop system shown in FIG. 6.

FIGS. 8–13 illustrate those embodiments of the invention using tape tabs as the male components of the fastening system. Otherwise, the structure of the diaper in these embodiments is the same as in FIGS. 2 and 6.

Figure 8:
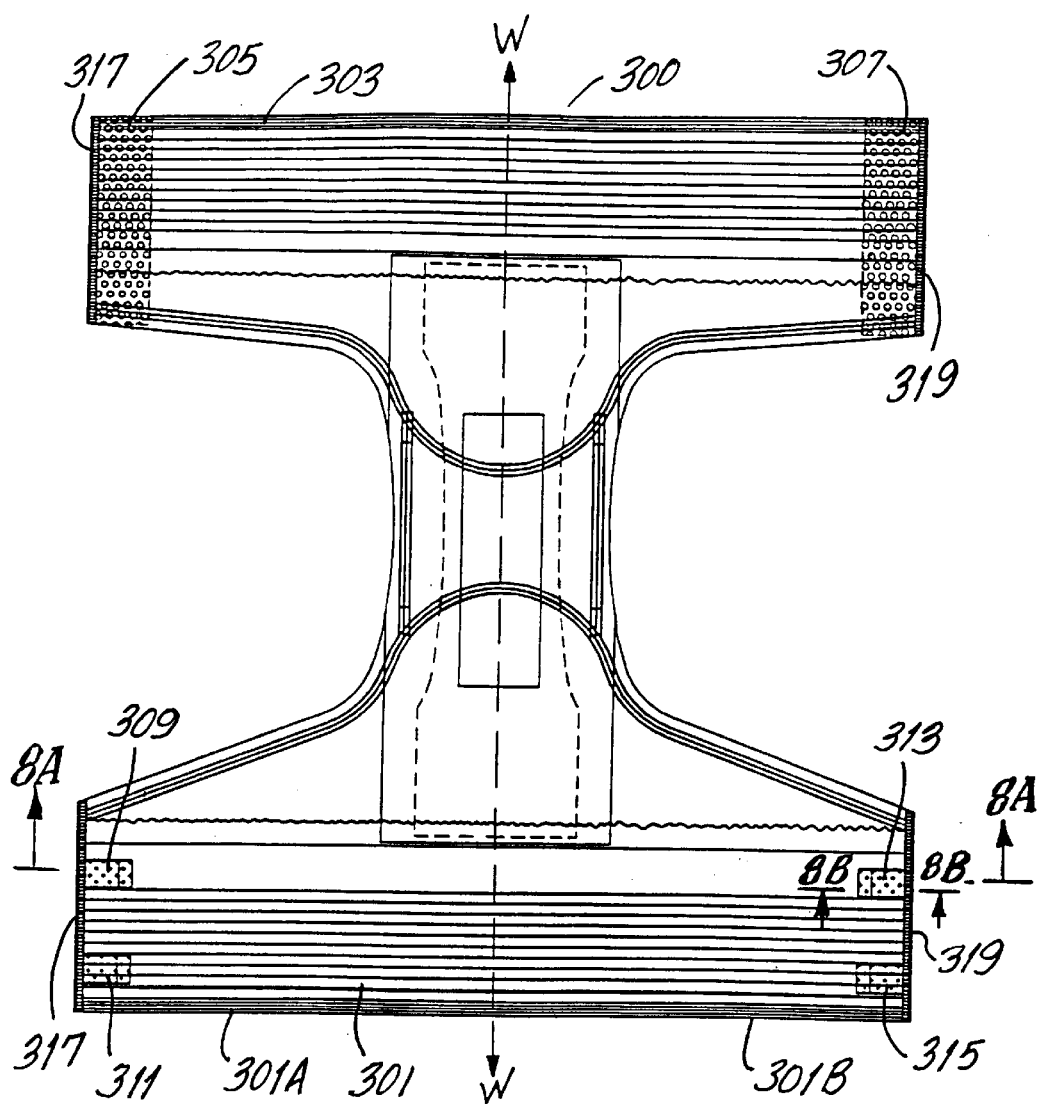
FIG. 8 is a view similar to FIG. 2 but using tape tabs with hooks in combination with loop fasteners wherein the tape tabs are located on the inside surface of the back waist.

Thus referring to FIG. 8 the diaper shown therein is generally designated as 300 comprising a back waist region 301 having opposed lateral wings, and a front waist region 303 having similar opposed lateral wings, relative to the longitudinal axis W—W of the diaper. The front waist region 303 comprises a pair of strips 305, 307 of loop material disposed on the outer surface near or at the lateral edge of the respective wings, and the back waist region 301 has tape tabs 309, 311, 313 and 315 attached thereto on the inside surface at or near the edge of the wings. As shown in FIGS. 8A and 8B the tape tab 313 has an adherent surface 313A attached to the back waist portion, a release paper 313B, a hook surface 313C opposite said adherent surface, and an adherent surface 313D for attaching said hook surface to the back waist region. The tape strip 313 has a finger lift 313E for lifting the adhesive strip in order to expose the hook surface. The release tape 313D and the finger lift 313E are optional and not strictly necessary.

In order to fasten the diaper the side seals 317, 319 are torn and the tape 313D is pulled away by lifting and pulling the finger lift 313E, the front waist region and the back waist region are then overlapped thereby engaging the hooks 309, 311, 313 and 315 onto the corresponding aligned loop strips 305 and 307. In the embodiment illustrated in FIG. 8 the front waist portion comprises the edge seal 317, 319 at each lateral edge of the front waist region, and edge seals 321, 323 at the lateral edges of the back waist region.

Figure 9:
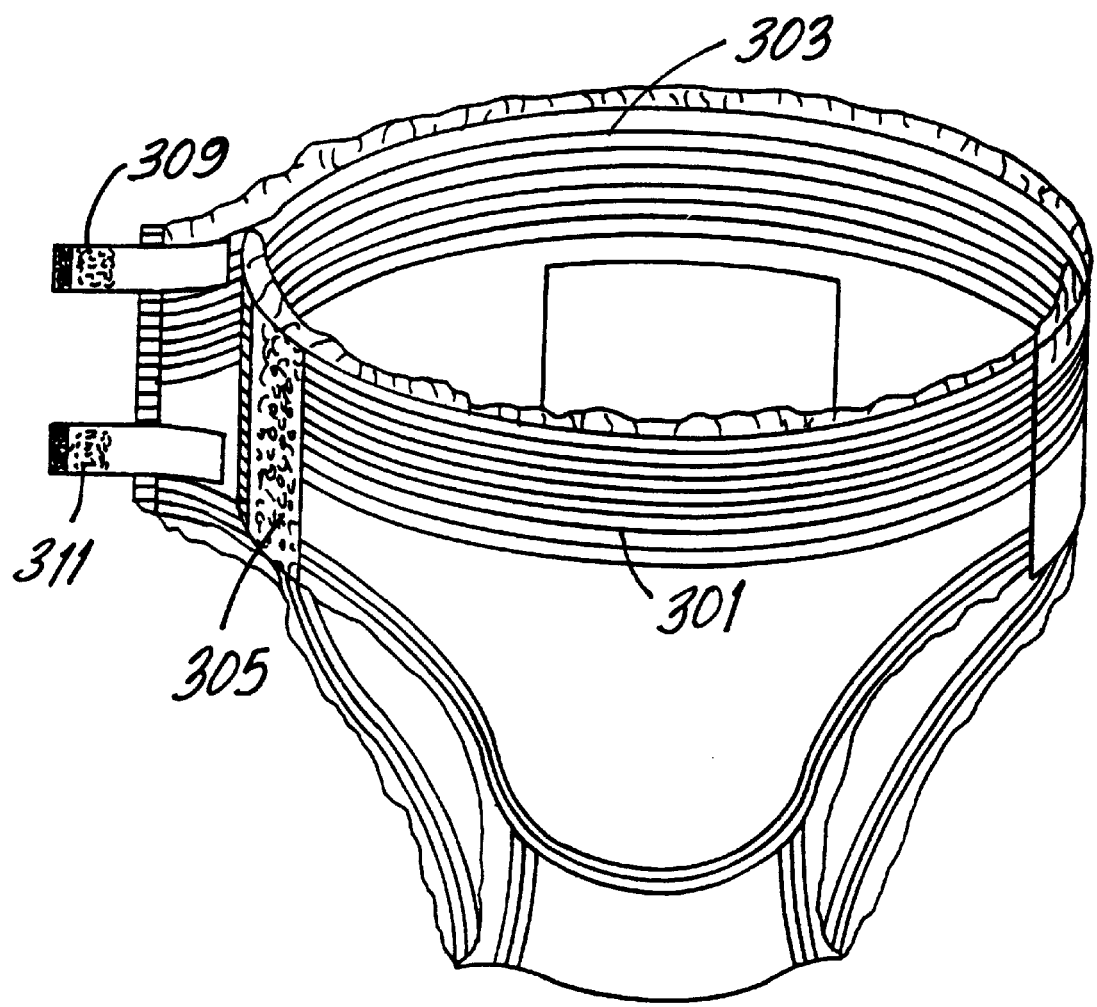
FIG. 9 is a perspective view of the diaper shown in FIG. 8 with the tape tabs pulled away from the loop fasteners and the diaper ready to wear.

FIG. 9 is a perspective view of the pull-up diaper shown in FIG. 8 and is similar to the diaper shown in FIG. 2 except for the provision of the tape tabs having hook surfaces. Otherwise, the structures of the two diapers are the same.

Figure 10:
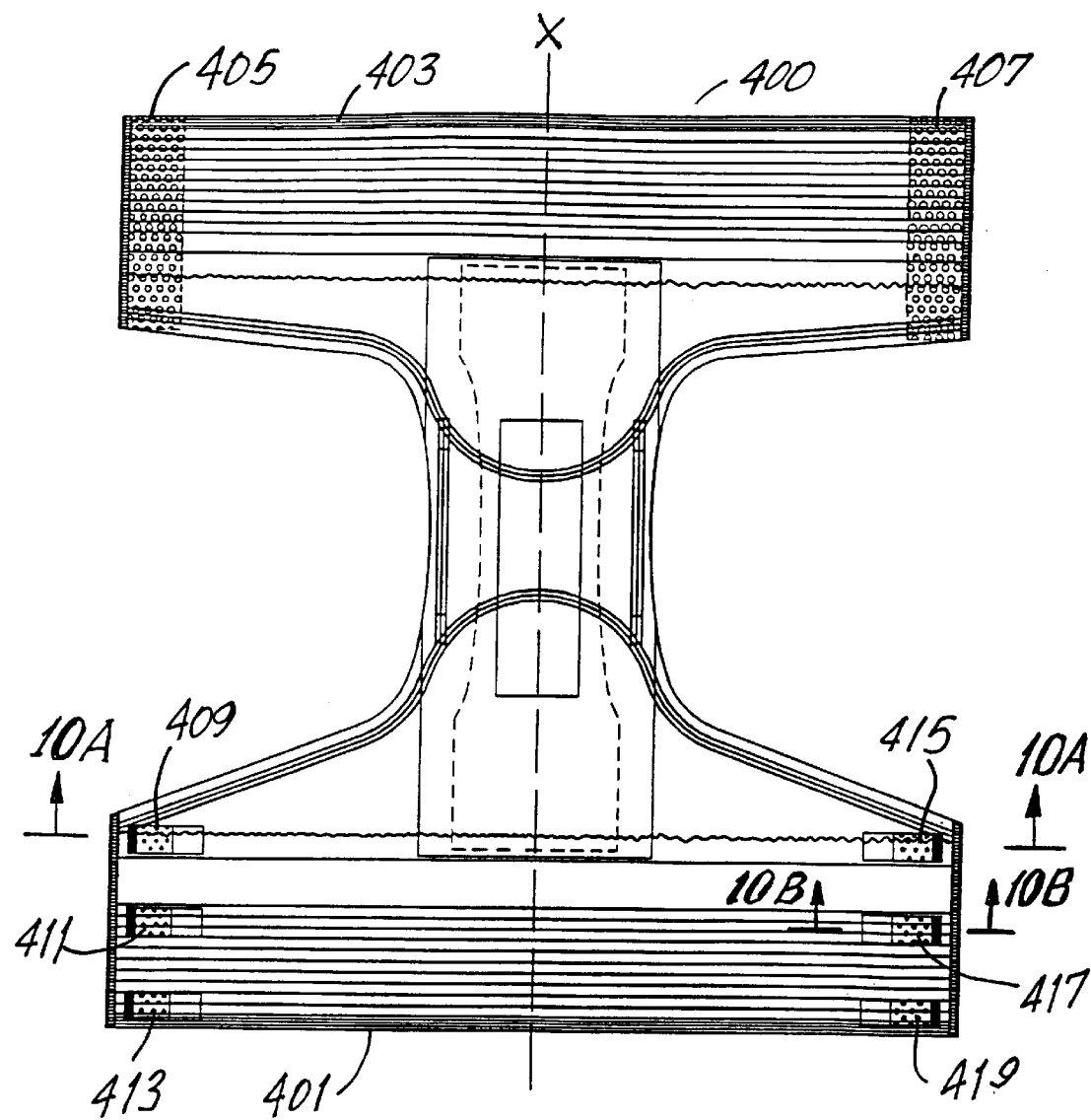
FIG. 10 is a stretched plan view of a pull-up diaper according to another embodiment of the present invention wherein the tape tabs are located on the outer surface of the back waist.

FIG. 10 is a stretched plan view of another embodiment of the invention similar to FIG. 8 but wherein the back waist region comprises three spaced apart tabs near the edge seal at each wing. Otherwise, the construction of the diaper is similar to the diaper shown in FIG. 8. Thus, the diaper shown in FIG. 10 is generally designated as 400 comprising a back waist region 401 having opposed lateral wings, and a front waist region having similar opposed lateral wings, relative to the longitudinal axis X—X of the diaper. The front waist region 403 comprises a pair of strips 405, 407 of loop material, each strip being disposed near or at the lateral edge of its respective wing, and the back waist region 401 has three tape tabs 409, 411, 413 attached thereto near the edge of one of said wings, and three tape tabs 415, 417, 419 attached near the other wings. As shown in FIG. 10, the external edges of the tape tabs are spaced inwardly relative to the edge of each wing. Each of the tape tabs is attached to the outside surface of the back waist region 401. Thus, referring to FIGS. 10A–10C, tape tab 415 has an adherent surface 415A and a backing film 415B for attaching the tape tab to the back waist region 401. A finger lift portion 415C permits lifting the backing film away from the waist's outer surface. The tape tab has a hook surface 415D and a release paper 415E. The remaining tape tabs, i.e., tape tabs 409, 411, 413, 417 and 419 have a structure similar to tape tab 415 and are positioned on the outer surface of the back waist region in the same manner. These tapes are attached to the back waist surface such that each finger lift edge is adjacent to the side seals.

The back waist region 401 and the front waist region 403 are fastened together in the same manner described in connection with the diaper shown in FIG. 8. Also, shown in FIG. 10, the front and back waist regions comprise edge seals at each lateral edge or wing.

The embodiment shown in FIG. 11 is similar to the embodiment shown in FIG. 10 with that the tape tabs located on the outer surface of the back waist region 503 of the diaper 500 except that the tapes are folded as shown in FIG. 11B. Referring to FIG. 11B which is an enlarged view of the tape tab 515, as shown therein, the tape tab construction is identical to the tapes shown in FIGS. 10, 10A, 10B and 10C. Thus, the tab has an adhesive surface 515A which is attached on the back side of the diaper and the remainder of the tape is folded to prevent the edges of the tape from interfering with the side seals. This tape also comprises a portion attached on the back side of the diaper waist, a release layer 521, a hook fastener 523 and a finger lift portion 521A.

Figure 12:
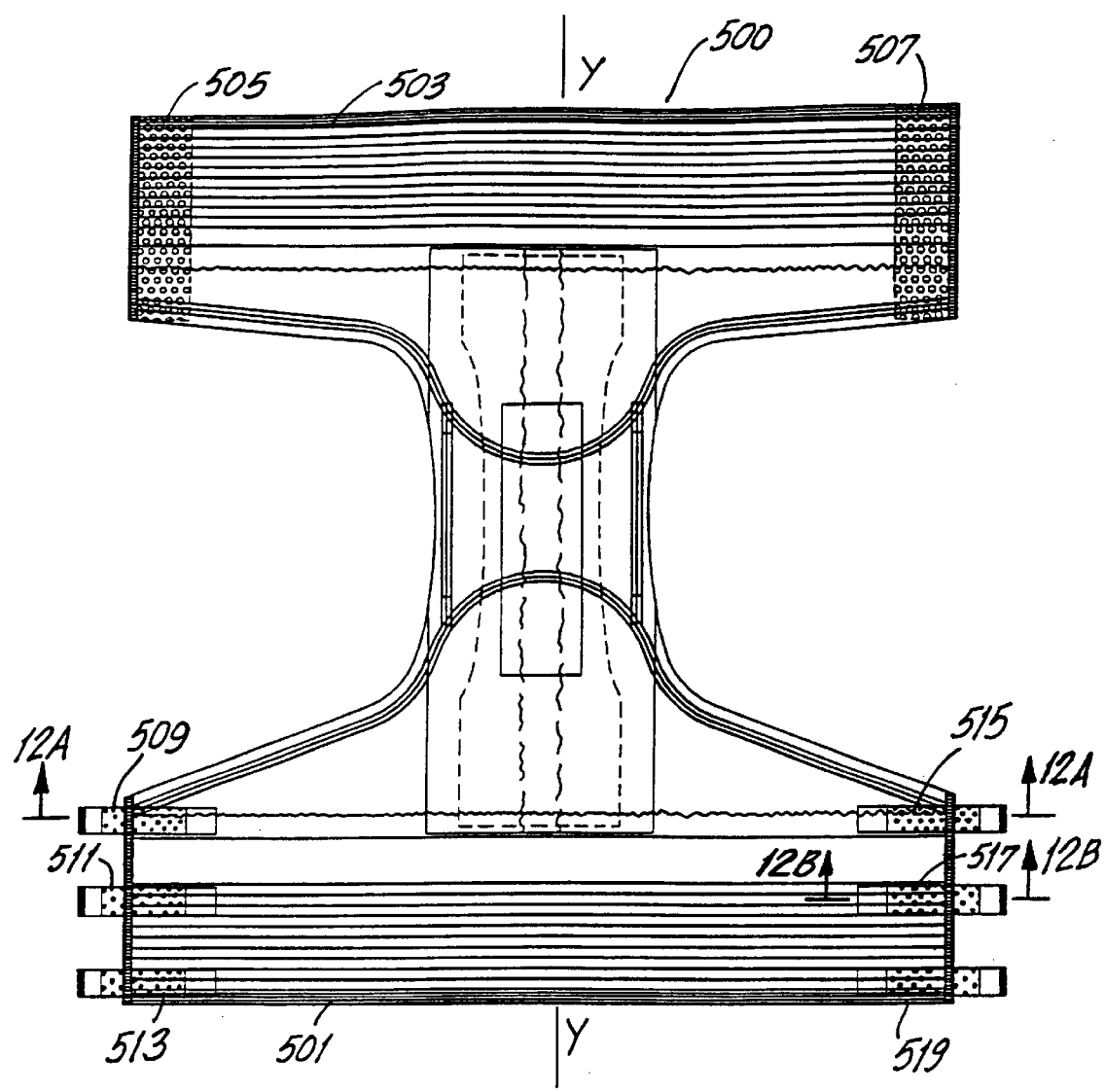
FIG. 12 is a stretched plan view of a different embodiment of the present invention similar to the embodiment illustrated in FIG. 10 with the tape tabs located on the outside surface of the back waist region and projecting outside of the lateral edges.

The embodiment shown in FIG. 12 is similar to the embodiment illustrated in FIG. 11 except that tape tabs attached to the back waist region project laterally beyond the edges of the respective wings. The diaper in FIG. 12 generally designated by 500 comprises a back waist region 501 having opposed lateral wings, a front waist region 503 having similar opposed lateral wings, a front waist region 503 having similar opposed lateral wings, relative to the longitudinal axis Y—Y of the diaper. The front waist region 503 comprises a pair of strips 505, 507 of loop material disposed near or at the lateral edges of the respective wings. The back waist region 501 has three tape tabs 509, 511, 513 attached thereto near the lateral edge of one of said wings, and the tape tabs 515, 517, 519 attached near or at the lateral edge of the other wing. Each of the tape tabs 509, 511, 513, 515, 517, 519 has a portion 509A, 511A, 513A, 515A, 517A and 519A, respectively, partly projecting beyond the lateral edge of each wing. These tapes are engaged with the respective loops on the back surface of the front waist region.

The manner of fastening the front and back waist regions to assemble the diaper is similar to the embodiments shown in FIG. 11. As shown in FIG. 12, if desired, side seals are provided at the respective lateral edges of each wing of the front and back waist regions. When one wishes to inspect or change the diaper, the tapes are disengaged from the loops, the side seal is torn and the diaper is inspected or changed.

Figure 13:
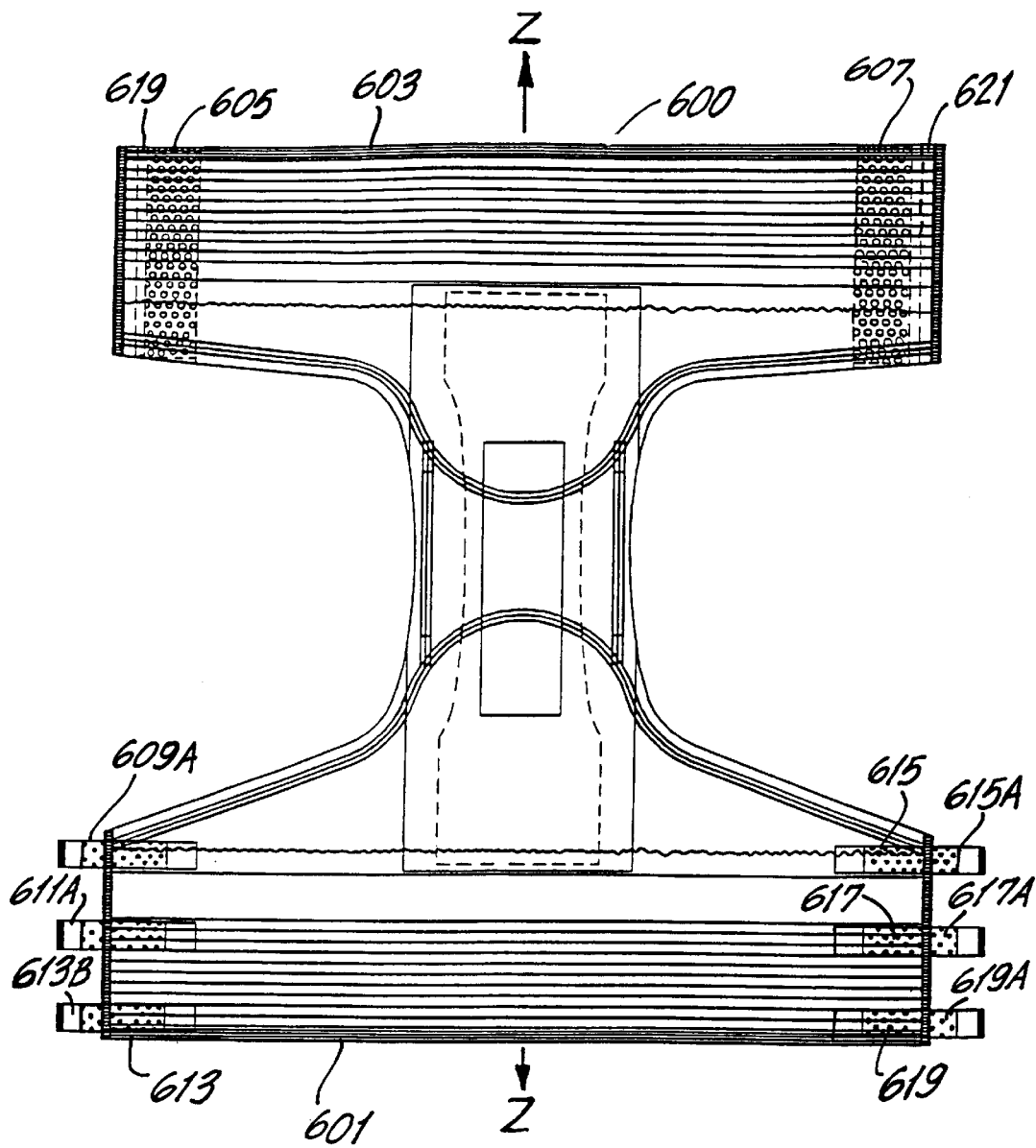
FIG. 13 is a stretched plan view of still another embodiment of the invention similar to FIG. 12 but having a weakened perforated line adjacent the side seal.

Another embodiment of the invention is illustrated in FIG. 13. The diaper shown in this figure is similar to FIG. 12 comprising a back waist region 601 having opposed lateral wings, and a front waist region 603 having similar opposed lateral wings, relative to the longitudinal axis Z—Z of the diaper. The front waist region 603 comprises a pair of strips 605, 607 disposed adjacent their respective lateral edges and spaced apart therefrom. The back waist region 601 has three tape tabs 609, 611, 613 attached thereto near the lateral edge of one of said wings, and tape tabs 615, 617, 619 attached near or at the lateral edge of the other wing. The tape tabs in this embodiment are similar to the tape tabs in the embodiment shown in FIG. 12 having laterally projecting portions 609A, 611A, 613A, 615A, 617A and 619A. The difference between these two embodiments is that in the diaper shown in FIG. 13, the loop strips 605, 607 are spaced inward relative to the edges of the respective lateral wings and the front waist region 603 comprises a weakened line such as a perforated line 621 and 623 disposed adjacent each of the loop strips 605, 607. Thus, when the diaper is fastened, the diaper may be inspected by tearing along the perforated lines to inspect the inside of the diaper for presence of urine or fecal material. Also, as shown in FIG. 13, the wings of the front and back waist regions have side seals for sealing the edges of the diaper.

The provision of perforated line in FIG. 13 permits tearing the diaper along this perforated line in order to inspect the diaper and engage the tapes with hooks to the loop surface. If the diaper has perforated lines as aforesaid, the provision of side seals is optional. Whether or not the diaper is provided with side seals, the tapes with a hook surface may be engaged onto the loop strips to form the ready-to-wear diaper, and this may be performed even during the manufacture of the diaper.

It is apparent from the foregoing detailed description and the several embodiments shown in the drawings that some modifications may be made in the construction of the diaper which are suggested thereby and hence are within the scope and contemplation of this invention.

What is claimed is:

1. An integral pull-up type absorbent article comprising:
   (a) a cover sheet;
   (b) a back sheet;
   (c) an absorbent layer disposed intermediate said cover sheet and said backsheet;
   (d) a pair of spaced apart leg openings;
   (e) a waist region comprising a front waist region and a back waist region, each of said regions having a laterally extending portion terminating in a generally vertical side edge;
   (f) a first hook strip disposed inwardly of one of said side edges, a first strip of loop material disposed inwardly relative to said other side edge, in one waist region,
   (g) a second hook strip adjacent said first hook strip and separated therefrom by a first tear line and a third hook strip adjacent said first strip of loop material and separated therefrom by a second tear line, in said waist region;
   (h) a third strip of loop material disposed inwardly relative to one of said side edges in said back waist region, and a fourth strip of loop material disposed inwardly relative to said other side edge in the other waist region,
      wherein, when said first and second tear lines are broken and said front and back waist regions are overlapped, each of said hook strips engages a corresponding aligned loop strip to fasten the diaper.

2. An integral pull-up type absorbent article as in claim 1 wherein each of said edges comprises a side seal.

3. An integral pull-up type absorbent article as in claim 2 wherein each of said side seals is adhesively secured to its respective side edge.

4. An integral pull-up type absorbent article as in claim 3, wherein said waist region is elasticated.

5. An integral pull-up type absorbent article as in claim 2 wherein said waist region is elasticated.

6. An integral pull-up type absorbent article as in claim 1 wherein said waist region is elasticated.

7. An integral pull-up type absorbent article comprising:
   (a) a cover sheet;
   (b) aback sheet;

(c) an absorbent layer disposed intermediate said cover sheet and said backsheet;

(d) a pair of spaced apart leg openings;

(e) a waist region comprising a front waist region and a back waist region, each of said regions having a laterally extending portion terminating in a generally vertical side edge;

(f) a first strip of loop material spaced apart relative to one of said side edges and a second strip of loop material spaced apart relative to the other end of said side edges, and (g) at least one tape tab attached to each side edge of said back waist region, each tape tab having a portion extending outwardly relative to its respective side edges and having a hook surface, wherein said front waist region comprises a tear line adjacent each of said strips of loop material and wherein when said front waist region and said back waist region overlap, the hook surface of each tape tab engages corresponding aligned strip of loop material.

8. An integral pull-up type absorbent article as in claim 7 wherein each of said side edges in the front waist region comprises a side seal.

9. An integral pull-up type absorbent article as in claim 8 wherein said waist region is elasticated.

10. An integral pull-up type absorbent article as in claim 7 wherein said waist region is elasticated.

* * * * *